US011000816B2

(12) United States Patent
Boaz et al.

(10) Patent No.: US 11,000,816 B2
(45) Date of Patent: May 11, 2021

(54) AMPHOTERIC ESTER SULFONATES

(71) Applicant: Eastman Chemical Company, Kingsport, TN (US)

(72) Inventors: Neil Warren Boaz, Kingsport, TN (US); Matthew Allen Boone, Gray, TN (US); Jennifer Michelle Lloyd, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 15/909,653

(22) Filed: Mar. 1, 2018

(65) Prior Publication Data

US 2018/0185801 A1   Jul. 5, 2018

Related U.S. Application Data

(62) Division of application No. 14/518,505, filed on Oct. 20, 2014, now Pat. No. 9,943,816.

(51) Int. Cl.
| | |
|---|---|
| *B01F 17/00* | (2006.01) |
| *C07D 211/06* | (2006.01) |
| *C07C 309/14* | (2006.01) |
| *C12P 13/00* | (2006.01) |
| *C12P 17/12* | (2006.01) |
| *C11D 1/92* | (2006.01) |
| *C07D 211/22* | (2006.01) |
| *C07D 211/46* | (2006.01) |

(52) U.S. Cl.
CPC ........ *B01F 17/0057* (2013.01); *C07C 309/14* (2013.01); *C07D 211/06* (2013.01); *C07D 211/22* (2013.01); *C07D 211/46* (2013.01); *C11D 1/92* (2013.01); *C12P 13/001* (2013.01); *C12P 17/12* (2013.01); *C12Y 301/01* (2013.01)

(58) Field of Classification Search
CPC . B01F 17/0057; C07C 309/14; C07D 211/06; C07D 211/22; C07D 211/46; C11D 1/92; C12P 13/00; C12P 17/12; C12Y 301/01
See application file for complete search history.

(56) References Cited

U.S. PATENT DOCUMENTS

| | | | |
|---|---|---|---|
| 2,781,349 A | 2/1957 | Mannheimer | |
| 3,001,997 A | 9/1961 | Mannheimer et al. | |
| 3,225,074 A | 12/1965 | Cowen et al. | |
| 3,280,178 A | 10/1966 | Barbour | |
| 3,280,179 A | 10/1966 | Ernst | |
| 3,915,882 A | 10/1975 | Nirschl et al. | |
| 4,259,191 A | 3/1981 | Wagner | |
| 4,352,913 A * | 10/1982 | Zondler | C07C 275/14 525/504 |
| 4,687,602 A | 8/1987 | Ballschuh et al. | |
| 4,879,204 A | 11/1989 | Ishigaki et al. | |
| 5,696,070 A | 12/1997 | Tachizawa et al. | |
| 5,851,982 A | 12/1998 | Sakata et al. | |
| 5,876,705 A | 3/1999 | Uchiyama et al. | |
| 5,972,877 A | 10/1999 | Tsuda et al. | |
| 6,365,560 B1 | 4/2002 | Chopra et al. | |
| 7,667,067 B1 | 2/2010 | Clendennen et al. | |
| 7,923,428 B2 | 4/2011 | Geffroy et al. | |
| 8,889,373 B2 | 11/2014 | Clendennen | |
| 8,900,625 B2 | 12/2014 | Damaj et al. | |
| 9,120,846 B2 | 9/2015 | Haymore | |
| 9,381,147 B2 | 7/2016 | Fevola et al. | |
| 2004/0101505 A1 | 5/2004 | Payne et al. | |
| 2006/0035807 A1 | 2/2006 | Kasturi et al. | |
| 2007/0042030 A1 | 2/2007 | Cevc | |
| 2010/0016198 A1 | 1/2010 | Bernhardt et al. | |
| 2010/0159393 A1 | 6/2010 | Fiebag et al. | |
| 2011/0300093 A1 | 12/2011 | Bendejacq et al. | |
| 2012/0040395 A1 | 2/2012 | Clendennen | |
| 2012/0277324 A1 | 11/2012 | Burk et al. | |
| 2014/0345483 A1 | 11/2014 | Imaizumi et al. | |

FOREIGN PATENT DOCUMENTS

| | | |
|---|---|---|
| CN | 102896879 A | 1/2013 |
| CN | 103 468 228 A | 12/2013 |
| DE | 1 240 872 B | 5/1967 |
| DE | 2 252 687 A1 | 5/1974 |
| DE | 274 332 A3 | 12/1989 |
| DE | 278 053 A1 | 4/1990 |
| DE | 278 054 A1 | 4/1990 |
| DE | 278 061 A1 | 4/1990 |
| EP | 0 205 626 A1 | 12/1986 |
| EP | 0205626 A1 | 12/1986 |
| EP | 2 818 930 A1 | 12/2014 |
| JP | 7-309724 A | 11/1955 |
| JP | S42 16415 A | 9/1967 |
| JP | S42 26523 B1 | 12/1967 |

(Continued)

OTHER PUBLICATIONS

CASREACT Search Results dated 2020-0817.*
Parris et al.; "Soap Based Detergent Formulation: XXIV. Sulfobetaine Derivatives of Fatty Amides[1]"; Journal of the American Oil Chemists' Society, vol. 54, pp. 294-296 (1977).
ASTM 1173-07; Standard Test Method for Foaming Properties of Surface-Active Agents.
Chattopadhyay et al.; "Fluorimetric Determination of Critical Micelle Concentration Avoiding Interference from Detergent Charge"; Analytical Biochemistry, vol. 139, pp. 408-412 (1984).
Copending U.S. Appl. No. 14/518,476, filed Oct. 20, 2014, Michael J. Fevola, et al.
Copending U.S. Appl. No. 14/518,517, filed Oct. 20, 2014, Neil Warren Boaz et al.
W.M. Wu et al., "Stereoisomers of N-substituted soft anticholinergics and their zwitterionic metabolite based on glycopyrrolate—syntheses and pharmacological evaluations," Pharmazie, vol. 63, pp. 200-209 (2008).

(Continued)

Primary Examiner — Robert H Havlin
(74) Attorney, Agent, or Firm — Phan Law Group PLLC

(57) ABSTRACT

Disclosed are a variety of amphoteric ester sulfonates, including 3-(N, N-dimethyl-cocoylpropylammonio-1-yl)-2-hydroxypropanesulfonate. These amphoteric ester sulfonates can be advantageously prepared in high yield and purity by a two-step chemoenzymatic process, and have excellent surfactant properties.

11 Claims, No Drawings

(56) References Cited

FOREIGN PATENT DOCUMENTS

| JP | S56 141375 A | 11/1981 |
|---|---|---|
| JP | 6-184934 A | 7/1994 |
| JP | 06184934 A | 7/1994 |
| JP | 10-97065 | 4/1998 |
| WO | WO 1998/033879 A1 | 8/1998 |
| WO | WO 2007/023336 A2 | 3/2007 |
| WO | 2007/059021 A1 | 5/2007 |
| WO | WO 2009/136396 A2 | 11/2009 |
| WO | 2010024356 A1 | 3/2010 |
| WO | WO 2011/114876 A1 | 9/2011 |
| WO | WO 2011/146595 A2 | 11/2011 |
| WO | 2012/024233 A2 | 2/2012 |
| WO | 2012/061098 A1 | 5/2012 |
| WO | 2012/080018 A2 | 6/2012 |
| WO | 2013/052087 A1 | 4/2013 |
| WO | 2016/064549 A1 | 4/2016 |

OTHER PUBLICATIONS

Copending U.S. Appl. No. 14/856,656, filed Sep. 17, 2015.
Copending U.S. Appl. No. 14/856,830, filed Sep. 17, 2015.
Int'l Search Report issued in Int'l Application No. PCT/US2015/053426.
Int'l Search Report issued in Int'l Application No. PCT/US2015/055263.
"Supplementary Examination Guidelines for Determining Compliance with 35 U.S.C. 112 and for Treatment of Related Issues in Patent Applications," Fed. Reg., vol. 76, No. 27, pp. 7162-7175 and slides 1, 64-67 (2011).
Boaz et al., Copending U.S. Appl. No. 15/283,739, filed Oct. 3, 2016.
Human English Translation of CN 103 468 228, pp. 1-9 (2013).
Int'l Search Report and Written Opinion issued in Int'l Appl. No. PCT/US2016/049972 dated Nov. 16, 2016.
English machine translation of DE 1 240 872 B, pp. 1-8 (May 24, 1967).
T.A. Spencer et al, "Zwitterionic Sulfobetaine Inhibitors of Squalene Synthase," J. Org. Chem., vol. 64, pp. 807-818 (1999).
C.Y. Guo et al., "Synthesis of Surface-Functionalized, Probe-Containing, Polymerized Vesicles Derived from Ammonium Bromide Surfactants," Langmuir, vol. 8, pp. 815-823 (1992).
S. Hashmi et al., "Supramolecular Interaction Controlled Diffusion Mechanism and Improved Mechanical Behavior of Hybrid Hydrogel Systems of Zwitterions and CNT," Macromolecules, vol. 45, pp. 9804-9815 (2012).
S. Abele et al., "Cationic and Zwitterionic Polymerizable Surfactants: Quaternary Ammonium Dialkyl Maleates 1. Synthesis and Characterization," Langmuir, vol. 15, pp. 1033-1044 (1999).
H. Liu et al., "Zwitterionic copolymer-based and hydrogen bonding-strengthened self-healing hydrogel," RSC Adv., vol. 5, pp. 33083-33088 (2015).
D. Kratzer et al., "A Synthetic Route to Sulfobetaine Methacrylates with Varying Charge Distance," Eur. J. Org. Chem., vol. 2014, pp. 8064-8071 (2014).
H. Tremblay et al., "One-pot synthesis of polyunsaturated fatty acid amides with anti-proliferative properties," Bioorg. Med. Chem. Lett., vol. 24, pp. 5635-5638 (2014).
N.N. Gandhi, "Applications of Lipase," JAOCS, vol. 74, pp. 621-634 (1997).
Int'l Search Report and Written Opinion issued in Int'l Application No. PCT/US2015/055258.
Int'l Search Report and Written Opinion issued in Int'l Appl. No. PCT/US2016/050470 dated Nov. 15, 2016.
C. Tastet et al., "Structure-efficiency relationships of zwitterionic detergents as protein solubilizers in tow-dimensional electrophoresis," Proteomics 2003, 3, 111-121.
Engiish machine translation of EP 0 205 626, pp. 1-5 (Dec. 30, 1986).
English machine translation of JP 06-184934, pp. 1-12 (Jul. 5, 1994).
English machine translation of JP0730724, pp. 1-26 (Unknown).
T. Morita et al., "In Situ Fluorescence Spectroscopic Studies of Energy Migration and Energy Transfer in the Monolayer of N-Ethylcarbazole-Containing Amphiphile," Langmuir 1998, 14, 171-175.
English Translation of WO 2010/024356 A1.
Huhtanen et al., "Inhibition of Clostridium botulinum by Aliphatic Amines and Long Chain Aliphatic Aminodiamides," J. Am. Oil Chem. Soc., 55, 854-855 (1978) (Huhtanen).

* cited by examiner

AMPHOTERIC ESTER SULFONATES

CROSS-REFERENCE TO RELATED APPLICATION

This application is a division of application Ser. No. 14/518,505 filed on Oct. 20, 2014; the entire content of which is hereby incorporated by reference.

PARTIES TO JOINT RESEARCH AGREEMENT

Inventions disclosed or claimed herein were made pursuant to a Joint Research Agreement between Eastman Chemical Company and Johnson & Johnson Consumer & Personal Products Worldwide, a division of Johnson & Johnson Consumer Companies Inc.

FIELD OF THE INVENTION

The invention generally relates to amphoteric ester sulfonates. More particularly, the invention relates to quaternary ammonium ester sulfonates, compositions of such compounds, uses of such compounds, and processes for making them.

BACKGROUND OF THE INVENTION

There is an increasing industrial and societal need for safer and more environmentally-friendly ingredients and methods for preparing those ingredients. In particular, it is highly desirable to provide methods that reduce or eliminate the use of irritating or allergenic starting materials, that employ biocompatible reagents, and that optimally use starting materials derived from a natural source or are "nature-equivalent." This is of urgent interest in consumer-facing industries, such as personal and household care.

One class of materials that may be approached in a "greener" manner is surfactants. Specifically, there is a need for new amphoteric surfactants that avoid using irritating or allergenic starting materials and that are made in a more environmentally-friendly manner.

Amphoteric (or zwitterionic) surfactants are used throughout the personal and household care industries. They are classified as specialty co-surfactants that complement the performance of primary surfactants. These co-surfactants also increase the mildness of the formulation by reducing irritation associated with purely ionic surfactants.

The most common zwitterionic sulfonate surfactants are amido-amine based materials produced by a multi-step process from coconut or palm kernel oil and N,N-dimethylamino-3-propylamine (DMAPA). Various patents (U.S. Pat. Nos. 3,280,179; 4,259,191) and publications (Parris et al., *J. Am. Oil Chem. Soc.*, Vol. 54, pp. 294-296 (1977)) detail commonly used preparation methods for these types of materials. The processes generally involve the amidation of fatty acids with DMAPA at high temperatures (150-175° C.). The intermediate fatty amino-amide is then reacted with a hydrophilic species, e.g., propane sultone or sodium 3-chloro-2-hydroxypropanesulfonate, to yield the final zwitterionic surfactant.

These processes have several drawbacks. For example, typical amidation processes require high temperatures for conversion and distillation to remove unreacted starting materials. These high reaction temperatures can generate by-products and impart color to the products, requiring additional steps to remove the by-products and the color.

Moreover, DMAPA is a known sensitizer, as is the corresponding amido-amine. Both are found in trace quantities in the final formulation.

Thus, there is a need for amphoteric/zwitterionic surfactants that can be prepared under milder conditions and without the use of DMAPA or a DMAPA amide.

The present invention addresses this need as well as others, which will become apparent from the following description and the appended claims.

SUMMARY OF THE INVENTION

The invention is as set forth in the appended claims.

Briefly, in one aspect, the present invention provides a compound having the formula 1:

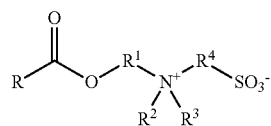

wherein
R is $C_3$-$C_{23}$ hydrocarbyl;
$R^1$ is $C_1$-$C_8$ hydrocarbyl;
$R^2$ and $R^3$ are each independently selected from the group consisting of $C_1$-$C_6$ alkyl, $C_1$-$C_6$ alkenyl, $C_1$-$C_6$ dienyl, $C_1$-$C_6$ trienyl, and $C_3$-$C_8$ cycloalkyl;
wherein at least two of $R^1$, $R^2$, and $R^3$ may be connected with the $N^+$ to form a heterocyclic ring; and
$R^4$ is $C_1$-$C_8$ hydrocarbyl.

In another aspect, the present invention provides a mixture comprising at least two compounds having the formula 1. The at least two compounds have at least one different R substituent.

In another aspect, the present invention provides a process for preparing the compound of formula 1. The process comprises:

(a) contacting an acid or ester of formula 2 with a dialkylamino-alcohol of formula 3:

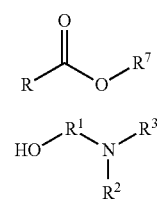

in the presence of an enzyme at conditions effective to form an intermediate of formula 4:

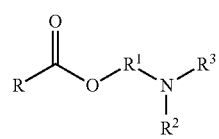

wherein R, $R^1$, $R^2$, and $R^3$ are as defined above in formula 1 and $R^7$ is hydrogen or $C_1$-$C_6$ alkyl; and (b) contacting the intermediate of formula 4 with a sulfonate alkylating agent at conditions effective to form the compound of formula 1.

In yet another aspect, the present invention provides a process for preparing a mixture comprising at least two compounds having the formula 1. The process comprises:

(a) contacting a mixture comprising at least two acids or esters of formula 2 with a dialkylamino-alcohol of formula 3:

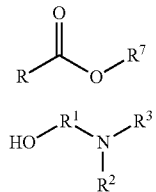

in the presence of an enzyme at conditions effective to form at least two intermediates of formula 4:

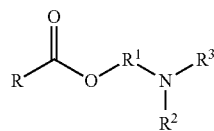

wherein
R, $R^1$, $R^2$, and $R^3$ are as defined above in formula 1,
$R^7$ is hydrogen or $C_1$-$C_6$ alkyl,
the at least two acids or esters of the formula 2 have different R substituents, and
the at least two intermediates of the formula 4 have different R substituents; and (b) contacting the intermediates of the formula 4 with a sulfonate alkylating agent at conditions effective to form the mixture of at least two compounds of the formula 1.

DETAILED DESCRIPTION OF THE INVENTION

In one aspect, the present invention provides a series of amphoteric ester sulfonate compounds having the formula 1:

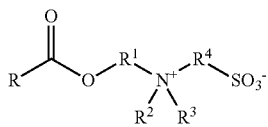

wherein
R is $C_3$-$C_{23}$ hydrocarbyl;
$R^1$ is $C_1$-$C_8$ hydrocarbyl;
$R^2$ and $R^3$ are each independently selected from the group consisting of $C_1$-$C_6$ alkyl, $C_1$-$C_6$ alkenyl, $C_1$-$C_6$ dienyl, $C_1$-$C_6$ trienyl, and $C_3$-$C_8$ cycloalkyl;
wherein at least two of $R^1$, $R^2$, and $R^3$ may be connected with the $N^+$ to form a heterocyclic ring; and
$R^4$ is $C_1$-$C_8$ hydrocarbyl.

As used herein, the term "hydrocarbyl" refers to mono- or di-valent hydrocarbon groups, depending on context. The term includes traditional hydrocarbyls such as alkyls, alkenes, alkynes, aryls, and cycloalkyls as well as hydrocarbylenes such as alkylenes, alkenylenes, alkynylenes, arylenes, and cycloalkylenes.

The hydrocarbyl group of R may be substituted or unsubstituted; branched or straight-chain; and saturated, mono-unsaturated, or poly-unsaturated. The hydrocarbyl group of R may also be substituted or unsubstituted $C_3$-$C_8$ cycloalkyl.

In a preferred embodiment, R is selected from substituted or unsubstituted, branched- or straight-chain, saturated $C_5$-$C_{19}$ alkyl; substituted or unsubstituted, branched- or straight-chain $C_5$-$C_{17}$ alkenyl; substituted or unsubstituted, branched- or straight-chain $C_5$-$C_{17}$ dienyl; and substituted or unsubstituted $C_3$-$C_8$ cycloalkyl.

The hydrocarbyl group of R may be substituted with one to five substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

As used herein, the terms "$C_1$-$C_6$ alkoxy," "$C_2$-$C_{06}$ alkoxycarbonyl," and "$C_2$-$C_{06}$ alkanoyloxy" are used to denote radicals corresponding to the structures —$OR^5$, —$CO_2R^5$, and —$OCOR^5$, respectively, where $R^5$ is substituted or unsubstituted $C_1$-$C_6$ alkyl.

As used herein, the terms "$C_1$-$C_{15}$ aminocarbonyl" and "$C_1$-$C_{15}$ amido" are used to denote radicals corresponding to the structures —$NHCOR^6$ and —$CONHR^6$, respectively, where $R^6$ is substituted or unsubstituted $C_1$-$C_{15}$ alkyl.

As used herein, the term "$C_3$-$C_8$ cycloalkyl" is used to denote a saturated, carbocyclic hydrocarbon radical having three to eight carbon atoms.

The hydrocarbyl group of $R^1$ may be branched- or straight-chain; substituted or unsubstituted; and saturated, mono-unsaturated, or poly-unsaturated $C_1$-$C_8$ hydrocarbyl. In one embodiment, $R^1$ is substituted or unsubstituted $C_3$-$C_8$ cycloalkylene.

In a preferred embodiment, $R^1$ is selected from branched or straight-chain $C_1$-$C_8$ alkylene, branched- or straight-chain $C_2$-$C_8$ alkenylene, and substituted or unsubstituted $C_3$-$C_8$ cycloalkylene. In another preferred embodiment, $R^1$ and $R^2$ combine to make a $C_3$-$C_8$ saturated, mono-unsaturated, or poly-unsaturated cyclic structure.

The divalent hydrocarbyl radicals of $R^1$ may be substituted with one to five substituents selected from the group consisting of $C_1$-$C_6$ alkoxy, $C_1$-$C_6$ carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

In one embodiment, R has at least two more carbon atoms than $R^1$.

The groups represented by $R^2$ and $R^3$ may be substituted or unsubstituted and branched or straight-chain.

$R^2$ and $R^3$ each independently may be substituted with one to three substituents selected from the group consisting of $C_1$-$C_6$ alkoxy, carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

In one embodiment, at least one of $R^2$ and $R^3$ is an alkyl, alkenyl, dienyl, or trienyl group. In another embodiment, at least one of $R^2$ and $R^3$ is a $C_3$-$C_8$ cycloalkyl group.

In a preferred embodiment, $R^2$ and $R^3$ are selected from straight-chain or branched $C_1$-$C_6$ alkyl and alkenyl.

At least two of $R^1$, $R^2$, and $R^3$ may be connected with the $N^+$ to form one or more heterocyclic rings. The resulting heterocycle (with the nitrogen) may be saturated, mono-unsaturated, or poly-unsaturated and may be a mono- or multi-cyclic ring structure. Examples of these heterocyclic structures include pyrrolidinium, piperidinium, pyridinium, quinolinium, tetrahydroquinolinium, indolinium, octahydroindolinium, acridinium, octahydroacridinium, and tetradecahydroacridinium.

The divalent hydrocarbyl radicals represented by $R^4$ may be straight-chain or branched and may be substituted or unsubstituted.

The hydrocarbyl group of $R^4$ may be substituted with one to three substituents selected from the group consisting of $C_1$-$C_6$ alkoxy, carboxyl, $C_1$-$C_{15}$ aminocarbonyl, $C_1$-$C_{15}$ amido, cyano, $C_2$-$C_6$ alkoxycarbonyl, $C_2$-$C_6$ alkanoyloxy, hydroxy, aryl, heteroaryl, thioether, $C_2$-$C_{10}$ dialkylamino, $C_3$-$C_{15}$ trialkylammonium, chlorine, and bromine.

In a preferred embodiment, $R^4$ is selected from substituted or unsubstituted $C_1$-$C_8$ alkylene.

Preferred examples of the compounds of the invention include those represented by the formula 1 where R is selected from the group consisting of $C_5$-$C_{19}$ alkyl, $C_5$-$C_{17}$ alkenyl, $C_5$-$C_{17}$ dienyl, and $C_3$-$C_8$ cycloalkyl; $R^1$ is selected from the group consisting of $C_1$-$C_8$ alkylene, $C_2$-$C_8$ alkenylene, and $C_3$-$C_8$ cycloalkylene; $R^2$ and $R^3$ are each independently selected from the group consisting of $C_1$-$C_6$ alkyl and $C_1$-$C_6$ alkenyl; $R^1$ and $R^2$ may be connected with the $N^+$ to form a $C_3$-$C_8$ heterocyclic structure; and $R^4$ is substituted or unsubstituted $C_1$-$C_8$ alkylene.

Preferred examples of the compounds of the invention also include those represented by the formula 1 where RCO— is a $C_6$ to $C_{20}$ acyl radical such as octanoyl, decanoyl, and lauroyl; $R^1$ is ethylene, 1,3-propylene, or 1,3-butylene; $R^2$ and $R^3$ are methyl; and $R^4$ is ethylene, 1,3-propylene, 1,4-butylene, or 2-hydroxy-1,3-propylene.

Preferred examples of the compounds of the invention further include those represented by the formula 1 where RCO— is a $C_6$ to $C_{20}$ acyl radical such as octanoyl, decanoyl, and lauroyl; $R^1$ and $R^2$ are connected with the $N^+$ to form a 3-piperidininum, a 4-piperidinium, a 3-piperidiniummethyl, a 4-piperidiniummethyl, a 3-pyridinum, a 4-pyridinium, a 3-pyridiniummethyl, or a 4-pyridiniummethyl group; $R^3$ is methyl; and $R^4$ is ethylene, 1,3-propylene, 1,4-butylene, or 2-hydroxy-1,3-propylene.

In various embodiments of the invention, the "$C_6$ to $C_{20}$ acyl radical" may be derived from coconut oil, hydrogenated coconut oil, hydrogenated and/or fractionated coconut oil fatty acids, palm kernel oil, hydrogenated palm kernel oil, or hydrogenated and/or fractionated palm kernel oil fatty acids. In which case, the resulting product may be a mixture of two or more compounds of the formula 1 where each compound has a different R substituent. For example, the "$C_6$ to $C_{20}$ acyl radical" may be derived from hydrogenated and stripped/fractionated coconut fatty acids. Coconut fatty acids typically include a mixture of fatty acids, such as $C_8$, $C_{10}$, $C_{12}$, $C_{14}$, $C_{16}$, and $C_{18}$ fatty acids. The fatty acids may be saturated, mono-unsaturated, or poly-unsaturated. The mixture may be hydrogenated to increase its melting point. In addition, the mixture may be stripped, for example, of the medium-chain fatty acids, such as $C_8$ and $C_{10}$ fatty acids, to yield a fraction of predominately long-chain fatty acids, such as $C_{12}$-$C_{18}$ fatty acids. These fractions (either the medium-chain or the long-chain, for example) may be used to produce the compounds of the invention. When such fractions are used, the reaction product would include a mixture of the compounds of the formula 1 where some compounds may have, for example, a $C_{12}$ acyl radical substituent while other compounds may have a $C_{14}$ acyl radical substituent, etc.

Thus, in another aspect, the present invention provides a mixture comprising at least two compounds having the formula 1:

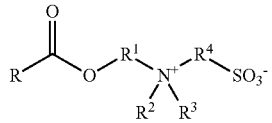

1 wherein
R is $C_3$-$C_{23}$ hydrocarbyl;
$R^1$ is $C_1$-$C_8$ hydrocarbyl;
$R^2$ and $R^3$ are each independently selected from the group consisting of $C_1$-$C_6$ alkyl, $C_1$-$C_6$ alkenyl, $C_1$-$C_6$ dienyl, $C_1$-$C_6$ trienyl, and $C_3$-$C_8$ cycloalkyl;
wherein at least two of $R^1$, $R^2$, and $R^3$ may be connected with the $N^+$ to form a heterocyclic ring; and
$R^4$ is $C_1$-$C_8$ hydrocarbyl. The at least two compounds have at least one different R substituent. In other words, the at least two compounds have different R substituents.

Preferred examples of the compounds in the mixture according to the invention include those represented by the formula 1 where RCO— is a $C_6$ to $C_{20}$ acyl radical such as octanoyl, decanoyl, cocoyl (acyl radicals derived from coconut fatty acids), hydrogenated cocoyl (acyl radicals derived from hydrogenated coconut fatty acids), and hydrogenated stripped cocoyl (acyl radicals derived from hydrogenated and fractionated/stripped coconut fatty acids); $R^1$ is ethylene, 1,3-propylene, or 1,3-butylene; $R^2$ and $R^3$ are methyl; and $R^4$ is ethylene, 1,3-propylene, 1,4-butylene, or 2-hydroxy-1,3-propylene.

Preferred examples of the compounds in the mixture according to the invention also include those represented by the formula 1 where RCO— is a $C_6$ to $C_{20}$ acyl radical such as octanoyl, decanoyl, cocoyl (acyl radicals derived from coconut fatty acids), hydrogenated cocoyl (acyl radicals derived from hydrogenated coconut fatty acids), and hydrogenated stripped cocoyl (acyl radicals derived from hydrogenated and fractionated/stripped coconut fatty acids); $R^1$ and $R^2$ are connected with the $N^+$ to form a 3-piperidininum, a 4-piperidinium, a 3-piperidiniummethyl, a 4-piperidiniummethyl, a 3-pyridinum, a 4-pyridinium, a 3-pyridiniummethyl, or a 4-pyridiniummethyl group; $R^3$ is methyl; and $R^4$ is ethylene, 1,3-propylene, 1,4-butylene, or 2-hydroxy-1,3-propylene.

In another aspect, the present invention provides a process for preparing amphoteric ester sulfonates. The process comprises:

(a) contacting an acid or ester of formula 2 with a dialkylamino-alcohol of formula 3:

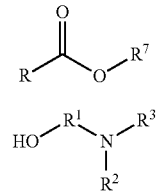

2

3 in the presence of an enzyme at conditions effective to form an intermediate of formula 4:

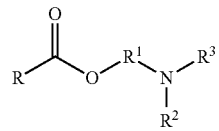

wherein R, $R^1$, $R^2$, and $R^3$ are as defined herein above and $R^7$ is hydrogen or $C_1$-$C_6$ alkyl; and (b) contacting the intermediate of formula 4 with a sulfonate alkylating agent at conditions effective to form the compound of formula 1.

The carboxylic acid or ester of the formula 2 may be obtained commercially or may be produced by any practical method, including the hydrolysis or solvolysis of triglycerides in the presence of water or a lower alcohol and a base, acid, or enzyme catalyst, as is known in the art. The preferred lower alcohols are $C_1$-$C_4$ alcohols, such as methanol, ethanol, 1-propanol, 2-propanol, 1-butanol, 2-butanol, and isobutanol.

The first step of the process involves a reaction of the dialkylamino-alcohol of the formula 3 with the acid or ester of the formula 2 in the presence of an enzyme to form the desired intermediate of the formula 4.

The enzymatic reaction of step (a) may be carried out without an added solvent or in the presence of an inert solvent. Examples of inert solvents include cyclic or acyclic ether solvents (such as diethyl ether, diisopropyl ether, tert-butyl methyl ether, and tetrahydrofuran), aromatic hydrocarbons (such as benzene, toluene, and xylene), aliphatic or alicyclic, saturated or unsaturated hydrocarbons (such as hexane, heptane, cyclohexane, and limonene), halogenated hydrocarbons (such as dichloromethane, dichloroethane, dibromoethane, tetrachloroethylene, and chlorobenzene), polar aprotic solvents (such as acetonitrile, dimethyl formamide, and dimethyl sulfoxide), and mixtures thereof.

In one embodiment, the enzymatic reaction is carried out in the absence of an added solvent.

In another embodiment, the enzymatic reaction is carried out in the presence of one or more aliphatic hydrocarbons as the solvent.

The enzymatic reaction may be carried out at a temperature from about −100° C. to the boiling point of the solvent (if employed), preferably from about 20 to 80° C., and more preferably from 50 to 70° C. The amount of the dialkylamino-alcohol 3 may be from 0.85 to 20 equivalents, based on the fatty acid or ester 2, preferably from 1 to 10 equivalents, and more preferably from 1 to 1.5 equivalents.

Step (a) in the process of the invention is desirably carried out in the presence of an enzyme effective to react the fatty acid or ester 2 with the dialkylamino-alcohol 3 to form the intermediate compound of the formula 4. Effective enzymes for this reaction include lipases. Examples of these enzymes include, but are not limited to, Lipase PS (from *Pseudomonas* sp), Lipase PS-C (from *Psuedomonas* sp immobilized on ceramic), Lipase PS-D (from *Pseudomonas* sp immobilized on diatomaceous earth), Lipoprime 50T, Lipozyme TL IM, Novozyme 435 (lipase from *Candida antarctica* immobilized on acrylic resin), and *Candida antarctica* lipase B immobilized on a porous fluoropolymer support as described in US 2012/0040395 A1. Immobilized enzymes have the advantage of being easily removed from the product and re-used.

The enzymatic reaction may be carried out with or without in situ water or alcohol by-product removal. The water or alcohol by-product can be removed by any known technique, such as chemically via an alcohol or water absorbent (e.g., molecular sieves) or by physical separation (e.g., evaporation). This by-product removal is preferably performed by evaporation, either by purging the reaction mixture with an inert gas such as nitrogen, argon, or helium, or by performing the reaction at reduced pressures, or both, as these conditions can afford >98% conversion of the fatty acid or ester 2 to the intermediate 4. The preferred pressure for carrying out the reaction ranges from 1 Torr (133.3 Pa) to ambient pressure, more preferably from 10 Torr (1,333 Pa) to ambient pressure, and most preferably from 50 Torr (6,665 Pa) to ambient pressure. Any organic solvent that is included in this step may or may not be removed along with the alcohol or water. Upon completion of the reaction in step (a), the intermediate 4 of the process may be isolated using methods known to those of skill in the art, e.g., extraction, filtration, or crystallization.

The second step in the process to generate the final product of the formula 1 involves reacting the intermediate compound of the formula 4 with a sulfonate alkylating agent. This step may also be carried out without an added solvent or in the presence of a solvent. Examples of solvents include water, alcohols and diols (such as methanol, ethanol, 1-propanol, 2-propanol, 1-butanol, 2-butanol, isobutanol, tert-butanol, tert-pentanol, ethylene glycol, 1,2-propanediol, and 1,3-propanediol), cyclic or acyclic ethers (such as diethyl ether, diisopropyl ether, tert-butyl methyl ether, and tetrahydrofuran), ether-alcohols (such as 2-methoxyethanol, 1-methoxy-2-propanol, ethylene glycol monobutyl ether, diethylene glycol monoethyl ether, diethylene glycol monopropyl ether, and diethylene glycol monobutyl ether), aromatic hydrocarbons (such as benzene, toluene, and xylene), aliphatic or alicyclic, saturated or unsaturated hydrocarbons (such as hexane, heptane, cyclohexane, and limonene), halogenated hydrocarbons (such as dichloromethane, dichloroethane, dibromoethane, tetrachloroethylene, and chlorobenzene), polar aprotic solvents (such as acetonitrile, dimethyl formamide, and dimethyl sulfoxide), and mixtures thereof. The preferred solvents include water, $C_2$-$C_5$ alcohols, ether-alcohols, and mixtures thereof.

The second step may be carried out at a temperature from about −100° C. to the boiling point of the solvent (if employed), preferably from about 25 to 150° C., more preferably from 50 to 150° C., and most preferably from 50 to 125° C.

The reaction in the second step may be carried out over a wide range of pressures. For example, the pressure may range from atmospheric to super-atmospheric, e.g., 5 atmospheres or higher.

The amount of sulfonate alkylating agent used is not particularly limiting. For example, the sulfonate alkylating agent may be used in an amount ranging from 0.75 to 20 equivalents based on the intermediate 4, preferably from 1 to 10 equivalents, and more preferably from 1 to 1.5 equivalents.

Optionally, a base is included in the reaction mixture of step (b). If included, the base may be chosen from metal hydroxides, metal carbonates, and metal bicarbonates. Preferred bases include sodium carbonate and sodium bicarbonate. The amount of base used can be from 0 molar equivalents to 1 molar equivalent, based on the ester of the formula 4. The preferred amount is a quantity sufficient to keep the reaction mixture slightly basic, generally a pH of 7.2 or greater.

Examples of sulfonate alkylating agents include, but are not limited to, 1,3-propanesultone, 1,4-butanesultone, sodium 2-chloroethanesulfonate, and sodium 3-chloro-2-hydroxypropanesulfonate.

Upon completion of the reaction in step (b), the intermediate 4 and the product 1 of the process may be isolated using methods known to those of skill in the art, e.g., extraction, filtration, or crystallization.

The process of the invention may be used to prepare a mixture of two or more compounds of the formula 1. If desired, a mixture of two or more carboxylic acids or esters of the formula 2 may be employed in the enzymatic reaction step. Such mixtures may be derived from coconut oil, hydrogenated coconut oil, hydrogenated and/or fractionated coconut oil fatty acids, palm kernel oil, hydrogenated palm kernel oil, or hydrogenated and/or fractionated palm kernel oil fatty acids. The enzymatic reaction step would yield a mixture of the intermediates of the formula 4. The mixture of intermediates 4 may then be reacted with the sulfonate alkylating agent to produce the mixture of compounds of the formula 1.

The amphoteric ester sulfonates of the formula 1 are particularly useful as surfactants. Thus, another aspect of the present invention relates to compositions of matter comprising one or more compounds of the formula 1 as surfactants. The compositions may contain from 0.001 to 20 weight percent of the compounds of the formula 1.

In particular, the amphoteric ester sulfonates of the invention possess both hydrophilic and hydrophobic regions, making them useful as surfactants in a number of formulated product applications, including personal care products, such as skin care, hair care, and other cosmetic products; household and industrial surface cleaners; laundry products; dish cleaners; disinfectants; metal working compositions; rust inhibitors; lubricants; oil field products; oil dispersants; agrochemicals; and dye dispersions. The amphoteric ester sulfonates can also be used as emulsifiers and thickening agents in emulsions. The amphoteric ester sulfonates can formulated into products as primary or secondary surface-active agents. Although their primary use is as humectants and foaming agents, the amphoteric ester sulfonates can also used for their anti-static and viscosity-controlling properties.

Such formulated products can contain from about 0.001 weight % to about 20 weight %, from about 0.01 weight % to about 15 weight %, or even from about 0.1 weight % to about 10 weight % of the amphoteric ester sulfonates.

The formulated products of the invention may include other surfactants in addition to the amphoteric ester sulfonates. These other surfactants can include anionic surfactants (such as alcohol ether sulfates, linear alkylbenzene sulfonates, and acyl isethionates), cationic surfactants (such as quaternary ammonium salts, amine oxides, and ester quats), amphoteric surfactants (such as betaines, amidobetaines, ester betaines, and amphoacetates), and non-ionic surfactants (such as alky polyglycosides, alcohol ethoxylates, and fatty alcanol amides). Such ingredients are known to those of skill in the art.

As noted, the formulated products of the invention can be cosmetic, skin, and hair care compositions. Those compositions may contain skin conditioning ingredients or cosmetically acceptable carriers in addition to the amphoteric ester sulfonates.

Such skin care ingredients/carriers include retinol, retinyl esters, tetronic acid, tetronic acid derivatives, hydroquinone, kojic acid, gallic acid, arbutin, α-hydroxy acids, niacinamide, pyridoxine, ascorbic acid, vitamin E and derivatives, aloe, salicylic acid, benzoyl peroxide, witch hazel, caffeine, zinc pyrithione, and fatty acid esters of ascorbic acid. Other skin care ingredients and carriers are known to those of skill in the art and may be used in the compositions of the invention.

Additional ingredients that may be included in these formulations include conditioning agents (such as polyquaterniums and panthenol), pearlizing agents (such as glycol distearate, distearyl ether, and mica), UV filters (such as octocrylene, octyl methoxycinnamate, benzophenone-4, titanium dioxide, and zinc oxide), exfoliation additives (such as apricot seeds, walnut shells, polymer beads, and pumice), silicones (such as dimethicone, cyclomethicone, and amodimethicone), moisturizing agents (such as petrolatum, sunflower oil, fatty alcohols, and shea butter), foam stabilizers (such as cocamide MEA and cocamide DEA), anti-bacterial agents such as triclosan, humectants such as glycerin, thickening agents (such as guar, sodium chloride, and carbomer), hair and skin damage repair agents (such as proteins, hydrolyzed proteins, and hydrolyzed collagen), and foam boosters such as cocamide MIPA. Such additional ingredients are known to those of skill in the art and may be used in the compositions of the invention.

Many personal care preparations are known in the art. They typically include acceptable carriers (such as water, oils and/or alcohols), emollients (such as olive oil, hydrocarbon oils and waxes, silicone oils, other vegetable, animal or marine fats or oils, glyceride derivatives, fatty acids or fatty acid esters), alcohols or alcohol ethers, lecithin, lanolin and derivatives, polyhydric alcohols or esters, wax esters, sterols, phospholipids, and the like. These same general ingredients can be formulated into liquids (such as liquid soaps, shampoos, or body washes), creams, lotions, gels, or into solid sticks by using different proportions of the ingredients and/or by inclusion of thickening agents such as gums or other forms of hydrophilic colloids. All such preparations may include the amphoteric ester sulfonates of the invention.

As used herein, the indefinite articles "a" and "an" mean one or more, unless the context clearly suggests otherwise. Similarly, the singular form of nouns includes their plural form, and vice versa, unless the context clearly suggests otherwise.

While attempts have been made to be precise, the numerical values and ranges described herein should be considered to be approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 50 to 100 is intended to describe and include all values within the range including sub-ranges such as 60 to 90 and 70 to 80.

The content of all documents cited herein, including patents as well as non-patent literature, is hereby incorporated by reference in their entirety.

To the extent that any incorporated subject matter contradicts with any disclosure herein, the disclosure herein shall take precedence over the incorporated content.

This invention can be further illustrated by the following examples of preferred embodiments thereof, although it will be understood that these examples are included merely for purposes of illustration and are not intended to limit the scope of the invention.

EXAMPLES

Example 1

Preparation of Methyl Cocoate

To a jar was added potassium hydroxide (1 g) and methanol (25 g). The solution was stirred for 1 hour. To a separate jar was added coconut oil (100 g). The solid was heated to a melt, and the KOH/MeOH solution was added, and the mixture was stirred overnight. The mixture was transferred to a separatory funnel and allowed to separate. The bottom/glycerol layer was removed. The top layer was filtered to afford a pale yellow oil (100 g). $^1$H NMR (300 MHz, CDCl$_3$) δ 3.65 (s, 3H), 2.28 (t, 2H), 1.60 (m, 2H), 1.24 (s, 16H), 0.86 (t, 3H).

Example 2

Preparation of 3-dimethylaminopropyl Cocoate

To a 50-mL conical bottom plastic vial was added methyl cocoate (8.72 g, 38.5 mmol), dimethylaminopropanol (4.76 g, 46.2 mmol, 1.2 eq), and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (9.2 g; 67% yield) without further purification. $^1$H NMR (300 MHz, CDCl$_3$) δ 4.10 (t, 2H), 2.30 (m, 4H), 2.21 (s, 6H), 1.78 (t, 2H), 1.60 (m, 2H), 1.24 (s, 16H), 0.86 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.6 min.

Example 3

Preparation of 3-(cocoyloxypropyldimethylammonio)-2-hydroxypropanesulfonate

To a 250-mL round bottom flask with a magnetic stir bar and a condenser was added 3-dimethylaminopropyl cocoate (10 g, 33.5 mmol), sodium 2-hydroxy-3-chloropropanesulfonate (ca. 90 wt %; 7.68 g, 35.2 mmol, 1.05 eq), sodium carbonate (355 mg; 3.35 mmol; 0.10 equiv), isopropanol (10 mL), and water (10 mL). The reaction mixture was heated in a 90° C. oil bath for 18 hours to afford 99.5 area % conversion according to HPLC analysis. The mixture was concentrated at reduced pressure to 28.31 g. Water (23 g) was added, the mixture was heated to afford solution, and the mixture was placed in a 65° C. oil bath, and the headspace was purged with nitrogen (1500 mL/min) for 2 hours to remove residual isopropanol to a weight of 33.78 g. Water (17.5 g) was added, and the mixture was stirred at 65° C. for 10 min to afford a homogeneous solution. The total weight of the solution was 51.11 g, indicating a 29 wt % solution of 3-(cocoyloxypropyldimethylammonio)-2-hydroxypropanesulfonate in water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.9 min.

Example 4

Preparation of 3-(cocoyloxypropyldimethylammonio)propanesulfonate

To a 100-mL round bottom flask with a magnetic stir bar and a condenser was added 3-dimethylaminopropyl cocoate (5 g, 16.7 mmol), 1,3-propanesultone (2.045 g, 16.7 mmol, 1.0 eq), and water (16.4 g). The reaction mixture was stirred at ambient temperature for 21 hours to afford 98.2 area % conversion according to HPLC analysis. The total weight of the solution was 23.4 g, indicating a 29.6 wt % solution of 3-(cocoyloxypropyldimethylammonio)propanesulfonate in water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.8 min.

Example 5

Preparation of 1-dimethylamino-2-propyl Cocoate

To a 250-mL 3-neck round bottom flask was added methyl cocoate (35 g, 160 mmol), 1-dimethylamino-2-propanol (16.49 g, 160 mmol, 1.0 eq), and Novozym 435 (2.62 g). The mixture was heated to 50° C. with stirring and sparged with nitrogen (500 mL/min). The reaction was monitored by GC and $^1$H NMR and additional 1-dimethylamino-2-propanol was added as necessary (lost due to evaporation) until >99 mol % conversion was obtained. The enzyme was removed by filtration, and the solid was washed with toluene. The filtrate was concentrated to afford 1-dimethylamino-2-propyl cocoate (42.66 g; 94% yield). $^1$H NMR (300 MHz, CDCl$_3$) δ 5.06 (m(6), 1H), 2.51 (dd, 1H), 2.31 (m, 3H); 2.26 (s, 6H), 1.60 (m, 2H), 1.22 (s, 16H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.6 min.

Example 6

Preparation of 3-(2-(cocoyloxy)propyldimethylammonio)-2-hydroxypropanesulfonate

To a 250-mL round bottom flask with a magnetic stir bar and a condenser was added 1-dimethylamino-2-propyl cocoate (5.0 g, 16.7 mmol), sodium 2-hydroxy-3-chloropropanesulfonate (ca. 90 wt %; 3.84 g, 17.6 mmol, 1.05 eq), sodium carbonate (177 mg; 1.67 mmol; 0.10 equiv), isopropanol (5 mL) and water (5 mL). The reaction mixture was heated in a 90° C. oil bath for 32 hours to afford 98.7 area % conversion according to HPLC analysis. The mixture was concentrated at reduced pressure, and water (23 g) was added. The mixture was heated to afford a solution, and the mixture was placed at ambient temperature and the headspace was purged with nitrogen (1000 mL/min) to small volume. The mixture was reconstituted with 10 mL of isopropanol and 4 mL of water to afford a clear solution. The total weight was 23.41 g, which indicated an approximately 31% solution of 3-(2-(cocoyloxy)propyldimethylammonio)-2-hydroxypropanesulfonate in isopropanol/water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.3 min.

Example 7

Preparation of Dimethylaminoethyl Cocoate

To a 50-mL conical bottom plastic vial was added ethyl cocoate (10 g, 38.5 mmol), dimethylaminoethanol (5.09 g, 57.7 mmol, 1.5 eq), and Novozym 435 (400 mg). A syringe was inserted through the cap and two additional holes were punched for gas to exit. Nitrogen was bubbled at a rate sufficient to mix the contents. The vial was placed in a heating block set to 65° C. The reaction was monitored by GC/MS to observe the disappearance of starting material. The reaction was complete after approximately 24 hours. The reaction mixture was allowed to cool. The Novozym 435 was removed by filtration to afford the product as a pale yellow oil (8 g; 73% yield) without further purification. $^1$H NMR (300 MHz, CDCl$_3$) δ 4.15 (t, 2H), 2.54 (t, 2H), 2.31 (t, 2H), 2.26 (s, 6H), 1.60 (m, 2H), 1.24 (s, 16H), 0.86 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.2 min.

Example 8

Preparation of 3-(cocoyloxyethyldimethylammonio)-2-hydroxypropanesulfonate

To a 100-mL round bottom flask with a magnetic stir bar and a condenser was added 2-dimethylaminoethyl cocoate (5.0 g, 17.6 mmol), sodium 2-hydroxy-3-chloropropanesulfonate (ca. 90 wt %; 4.41 g, 20.2 mmol, 1.15 eq), sodium carbonate (186 mg; 1.76 mmol; 0.10 equiv), isopropanol (5 mL), and water (5 mL). The reaction mixture was heated in a 90° C. oil bath for 18 hours to afford 95.3 area % conversion according to HPLC analysis. The mixture was concentrated with a headspace purge and diluted with water to about 30% concentration to afford a heterogeneous mixture. The material was concentrated with a headspace nitrogen purge at 60° C. and reconstituted with isopropanol and water to afford a clear solution. The total weight was 26.10 g, which indicated an approximately 27% solution of 3-(cocoyloxyethyldimethylammonio)-2-hydroxypropanesulfonate in isopropanol/water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.6 min.

Example 9

Preparation of 3-(cocoyloxypropyldimethylammonio)butanesulfonate

To a 250-mL round bottom flask with a magnetic stir bar and a condenser was added 3-dimethylaminopropyl cocoate (10.0 g, 33.5 mmol), 1,4-butanesultone (4.56 g, 33.5 mmol, 1.0 eq), isopropanol (10 mL), and water (10 mL). The reaction mixture was stirred and heated at 80° C. for 24 hours to afford 99.1 area % conversion according to HPLC analysis. The total weight of the solution was 31.27 g, indicating an approximately 46 wt % solution of 3-(cocoyloxypropyldimethylammonio)butanesulfonate in isopropanol/water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.75 min.

Example 10

Preparation of 3-(cocoyloxyethyldimethylammonio)propanesulfonate

To a 100-mL round bottom flask with a magnetic stir bar and a condenser was added 2-dimethylaminoethyl cocoate (3.5 g, 12.3 mmol), 1,3-propanesultone (1.50 g, 12.3 mmol, 1.0 eq), isopropanol (3.5 mL), and water (3.5 mL). The reaction mixture was stirred at ambient temperature for 36 hours to afford 99.3 area % conversion according to HPLC analysis. The total weight of the solution was 10.87 g, indicating approximately a 46 wt % solution of 3-(cocoyloxyethyldimethylammonio)-propanesulfonate in isopropanol/water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.5 min.

Example 11

Preparation of N-methyl-4-piperidinyl Cocoate

To a 250-mL round bottom flask with a magnetic stir bar was added methyl cocoate (25 g, 117 mmol), 4-hydroxy-N-methylpiperidine (17.46 g, 152 mmol), heptane (10 mL), and Novozym 435 (2.50 g). A Dean-Stark apparatus was placed onto the flask and the mixture was heated to 65° C. The heptane azeotrope was utilized to remove methanol by reducing the pressure until the azeotrope distilled overhead into the Dean-Stark trap to return the heptane to the reaction vessel. After 1.5 hrs, the reaction was stopped. After the mixture was cooled to ambient temperature, Novozym 435 was recovered by filtration. After heating to 65° C., nitrogen was bubbled through the mixture to remove any unreacted 4-hydroxy-N-methylpiperidine. $^1$H NMR analysis indicated 98 mol % conversion to the product, which was isolated as a yellow oil (29.57 g; 82% yield). $^1$H NMR (300 MHz, CDCl$_3$) δ 4.78 (m, 1H), 2.66 (m, 2H), 2.32-2.22 (m, 7H); 1.95-1.86 (m, 2H); 1.77-1.58 (m, 4H); 1.38-1.25 (m, 18H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.2 min.

Example 12

Preparation of 3-(4-(cocoyloxy)-1-methylpiperidinium-1-yl)-2-hydroxypropanesulfonate To a 100-mL round bottom flask with a magnetic stir bar and a condenser was added N-methyl-4-piperidinyl cocoate (5.0 g, 16.2 mmol), sodium 2-hydroxy-3-chloropropanesulfonate (ca. 90 wt %; 3.70 g, 16.95 mmol, 1.05 eq), sodium carbonate (171 mg; 1.62 mmol; 0.10 equiv), isopropanol (5 mL), and water (5 mL). The reaction mixture was heated in a 90° C. oil bath for 24 hours to afford 98.5 area % conversion according to HPLC analysis. The total weight of the solution was 15.50 g, indicating approximately a 46 wt % solution of 3-(4-(cocoyloxy)-1-methylpiperidinium-1-yl)-2-hydroxypropanesulfonate in isopropanol/water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.9, 5.2 min.

Example 13

Preparation of N-methyl-4-piperdinylmethyl Cocoate

To a 250-mL round bottom flask was added methyl cocoate (50 g, 233 mmol), 4-hydroxymethyl-N-methylpiperidine (33.2 g, 257 mmol), and Novozym 435 (5.0 g). The flask was fitted with a septum, and a needle was inserted to vent. Nitrogen was bubbled at a rate sufficient to mix the contents. The reaction mixture was heated to 50° C. After approximately 15 hours, $^1$H NMR analysis indicated that the reaction was complete. The reaction mixture was allowed to cool. The Novozym 435 was removed by filtration. The material was taken up in diethyl ether (250 mL) and subsequently washed with water (250 mL×2). After drying with $Na_2SO_4$, the mixture was filtered and concentrated. After dissolving in small amount of dichloromethane, the mixture was filtered through a short plug of magnesol and concentrated to afford the product as a pale yellow oil (57.89 g; 77% yield). $^1$H NMR (300 MHz, $CDCl_3$) δ 3.93 (d, 2H), 2.86 (m, 2H), 2.32-2.27 (m, 5H), 1.91 (t, 3H), 1.73-1.56 (m, 5H), 1.41-1.23 (m, 19H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 4.2 min.

Example 14

Preparation of 3-((4-(cocoyloxy)methyl)-1-methylpiperidinium-1-yl)-2-hydroxypropanesulfonate To a 100-mL round bottom flask with a magnetic stir bar and a condenser was added N-methyl-4-piperidinyl cocoate (4.5 g, 13.9 mmol), sodium 2-hydroxy-3-chloropropanesulfonate (ca. 90 wt %; 3.19 g, 14.6 mmol, 1.05 eq), sodium carbonate (147 mg; 1.39 mmol; 0.10 equiv), isopropanol (4.5 mL), and water (4.5 mL). The reaction mixture was heated in a 90° C. oil bath for 15 hours to afford complete conversion according to HPLC analysis. The total weight of the solution was 14.20 g, indicating approximately a 45 wt % solution of 3-((4-(cocoyloxy)methyl)-1-methylpiperidinium-1-yl)-2-hydroxypropanesulfonate in isopropanol/water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.2, 5.5 min.

Example 15

Preparation of Dimethylaminopropyl Laurate

Lauric acid (600 g; 3.0 mol), 3-dimethylaminopropanol (371 g; 3.59 mol; 1.2 equiv), Novozym 435 (30 g), and heptane (267 mL) were combined and heated to 65° C. The heptane azeotrope was utilized to remove water by reducing the pressure until the azeotrope distilled overhead into a Dean-Stark trap to return the heptane to the reaction vessel. The reaction was allowed to proceed until GC analysis indicated >99 area % conversion of lauric acid to the 3-dimethylaminopropyl ester. The enzyme was removed by filtration, and the filtrate was concentrated. The concentrate was purged with nitrogen overnight at 60° C. to remove excess 3-dimethylaminopropanol. $^1$H NMR (300 MHz, $CDCl_3$) δ 4.09 (t, 2H), 2.32 (t, 2H), 2.27 (t, 2H); 2.20 (s, 6H); 1.78 (m(5), 2H); 1.59 (m, 2H), 1.26 (m, 16H), 0.86 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.6 min.

Example 16

Preparation of 3-(lauroyloxypropyldimethylammonio)-2-hydroxypropanesulfonate

To a 100-mL round bottom flask with a magnetic stir bar and a condenser was added 3-dimethylaminopropyl laurate (5 g, 17.5 mmol), sodium 2-hydroxy-3-chloropropanesulfonate (ca. 90 wt %; 4.40 g, 20.1 mmol, 1.15 eq), sodium carbonate (186 mg; 1.75 mmol; 0.10 equiv), isopropanol (15 mL), and water (2.5 mL). The reaction mixture was heated in a 90° C. oil bath for 11 hours to afford 99.9 area % conversion according to HPLC analysis.

The material was filtered, and the filtrate was concentrated at reduced pressure to 11.29 g. Water (14 g) was added, the mixture was heated to afford a solution, the mixture was placed in a 65° C. oil bath, and the headspace was purged with nitrogen to remove residual isopropanol to a weight of 16.00 g. Water (6.93 g) was added, and the mixture was stirred at 65° C. for 10 min to afford a homogeneous solution. The total weight of the solution was 22.93 g, indicating a 32 wt % solution of 3-(cocoyloxypropyldimethylammonio)-2-hydroxypropanesulfonate in water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.9 min.

Example 17

Preparation of N-methyl-4-piperdinyl Laurate

To a 250-mL round bottom flask with a magnetic stir bar was added methyl laurate (25 g, 117 mmol), 4-hydroxy-N-methylpiperidine (17.46 g, 152 mmol), heptane (10 mL), and Novozym 435 (2.50 g). A Dean-Stark apparatus was placed onto the flask, and the mixture was heated to 65° C. The heptane azeotrope was utilized to remove water by reducing the pressure until the azeotrope distilled overhead into the Dean-Stark trap to return the heptane to the reaction vessel. After 3 hrs, GC analysis indicated 98.7 area % conversion. The reaction was allowed to cool to ambient temperature. Novozym 425 was recovered by filtration. The mixture was taken up in diethyl ether (100 mL) and washed with water (100 mL). The organics were dried with $Na_2SO_4$. After filtration, the volatiles were removed under reduced pressure to afford a pale yellow oil that solidified upon standing (32.09 g; 92% yield). $^1$H NMR (300 MHz, $CDCl_3$) δ 4.78 (m, 1H), 2.65 (m, 2H), 2.32-2.22 (m, 7H); 1.95-1.85 (m, 3H); 1.77-1.57 (m, 4H); 1.35-1.23 (m, 17H), 0.88 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.2 min.

Example 18

Preparation of 3-(4-(lauroyloxy)-1-methylpiperidinium-1-yl)-2-hydroxypropanesulfonate To a 100-mL round bottom flask with a magnetic stir bar and a condenser was added N-methyl-4-piperidinyl laurate (3.0 g, 10.0 mmol), sodium 2-hydroxy-3-chloropropanesulfonate (ca. 90 wt %; 2.42 g, 11.1 mmol, 1.1 eq), sodium carbonate (107 mg; 1.0 mmol; 0.10 equiv), 1-methoxy-2-propanol (9 mL), and water (1.5 mL). The reaction mixture was heated to reflux (102° C. oil bath) for 15 hours to afford 99.5 area % conversion according to HPLC analysis. The mixture was concentrated to about half the original volume to afford a precipitate. The precipitate was removed by filtration, and the cake was washed with isopropanol. The filtrate was stripped to small volume and water (17.2 g) was added. The mixture was heated to 65° C., and the headspace was purged with nitrogen for several hours to remove any remaining isopropanol and 1-methoxy-2-propanol to afford 12.22 g of the product mixture. Water was added to afford a total weight of the solution 14.40 g, indicating approximately a 30 wt % solution of 3-(4-(lauroyloxy)-1-methylpiperidinium-1-yl)-2-hydroxypropanesulfonate in water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.7, 5.0 min.

Example 19

Preparation of 3-cocoyloxymethyl-N-methylpiperidine

To a 250-mL round bottom flask with a magnetic stir bar was added methyl cocoate (69.0 g, 322 mmol), 3-hydroxymethyl-N-methylpiperidine (49.89 g, 386 mmol), and Novozym 435 (10.0 g). The flask was fitted with a septum, and a needle was inserted to vent. Nitrogen was bubbled at a rate sufficient to mix the contents. The mixture was heated to 65° C. After 12 hrs, the sparge rate was increased. At 19.5 hrs, $^1$H NMR analysis indicated that the reaction was complete. After filtration, the mixture was taken up in $Et_2O$ (750 mL) and subsequently washed with water (250 mL×2). The organics were dried with $Na_2SO_4$. After filtration, the volatiles were removed under reduced pressure to afford the product as a pale yellow oil (91.67 g; 88% yield). $^1$H NMR (300 MHz, $CDCl_3$) δ 3.98 (m, 1H), 3.86 (m, 1H), 2.80 (m, 2H), 2.28 (t, 2H), 2.25 (s, 3H), 2.03-1.82 (m, 2H), 1.72-1.55 (m, 5H), 1.33-1.18 (m, 18H), 0.87 (t, 3H).

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.7 min.

Example 20

Preparation of 3-(3-cocoyloxymethyl)-1-methylpiperidinium-1-yl)-2-hydroxypropanesulfonate To a 100-mL round bottom flask with a magnetic stir bar and a condenser was added 3-cocoyloxymethyl-N-methylpiperidine (5.0 g, 16.1 mmol), sodium 2-hydroxy-3-chloropropanesulfonate (ca. 90 wt %; 3.47 g, 15.9 mmol, 1.0 eq), sodium carbonate (107 mg; 1.0 mmol; 0.10 equiv), 1-methoxy-2-propanol (15 mL), and water (2.5 mL). The reaction mixture was heated to reflux (102° C. oil bath) for 15.5 hours to afford 99.3 area % conversion according to HPLC analysis. The mixture was cooled to ambient temperature, and the solids were removed by filtration. The total weight of the yellow solution was 21.67 g, indicating approximately a 33 wt % solution of 3-(3-(cocoyloxymethyl)-1-methylpiperidinium-1-yl)-2-hydroxypropanesulfonate in 1-methoxy-2-propanol and water. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ (laurate ester) 5.1, 5.4 min.

Example 21

Preparation of N-methyl-4-piperdinyl Hydrogenated Cocoate

To a round bottom flask with a magnetic stir bar was added methyl hydrogenated cocoate (30.3 g, 134 mmol), 4-hydroxy-N-methylpiperidine (20.0 g, 174 mmol; 1.3 equiv), heptane (10.5 mL), and Novozym 435 (3 g). A Dean-Stark apparatus was placed onto the flask, the mixture was heated to 65° C., and the reaction was placed under vacuum to distill the methanol/heptane azeotrope (heptane was returned to the flask via the Dean-Stark apparatus). The reaction was conducted until GC analysis indicated 99 area % conversion to the ester. The reaction was allowed to cool to ambient temperature, and the solids (Novozym 435) were removed by filtration and washed with heptane. The filtrate was washed with water and dried with $Na_2SO_4$. After filtration, the volatiles were removed under reduced pressure to afford the products as a pale yellow oil (41.1 g; 99% yield). $^1$H NMR analysis was consistent with the product structure.

HPLC (150×4.6 mm Zorbax SB-C8 column, 75:25 (v:v) methanol:water (containing 0.1 vol % trifluoroacetic acid)

for 10 min, gradient to 100% methanol over 1 min, held at 100% methanol for 9 min, ELSD detection): $t_R$ 4.2 min (laurate).

Example 22

Preparation of 3-(4-(hydrogenated cocoyloxy)-1-methylpiperidinium-1-yl)-2-hydroxypropane-sulfonate To a 100-mL round bottom flask with a magnetic stir bar and a condenser was added N-methyl-4-piperidinyl hydrogenated cocoate (7.50 g, 24.18 mmol), sodium 2-hydroxy-3-chloropropanesulfonate (ca. 90 wt %; 5.81 g, 26.6 mmol, 1.1 eq), sodium carbonate (256 mg; 2.42 mol; 0.10 equiv), and 1-methoxy-2-propanol (22.5 mL). The reaction mixture was heated to 110° C. for 24 hours to afford 99.6 area % conversion to product according to HPLC analysis. The mixture was filtered while warm (60° C.) to remove any precipitated solids, and the solids were washed with isopropanol. The combined filtrate and washes were concentrated at reduced pressure and in vacuo to afford 12.31 g of the product as an off-white solid. A portion (10.89 g) of this material was dried in a vacuum oven to afford 10.12 g of material that assayed at 93.5 wt % 3-(4-(hydrogenated cocoyloxy)-1-methylpiperidinium-1-yl)-2-hydroxypropane-sulfonate by HPLC. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.7, 5.0 min (laurate).

Example 23

Preparation of N-methyl-4-piperdinyl Hydrogenated Stripped Cocoate

To a round bottom flask with a magnetic stir bar was added hydrogenated stripped coconut fatty acids (29.7 g, 134 mmol), 4-hydroxy-N-methylpiperidine (20.0 g, 174 mmol; 1.3 equiv), heptane (10.5 mL), and Novozym 435 (3 g). A Dean-Stark apparatus was placed onto the flask, the mixture was heated to 65° C., and the reaction was placed under vacuum to distill the water/heptane azeotrope (heptane was returned to the flask via the Dean-Stark apparatus). The reaction was conducted until GC analysis indicated 99 area % conversion to the ester. The reaction was allowed to cool to ambient temperature, and the solids (Novozym 435) were removed by filtration and washed with heptane. The filtrate was washed with water and dried with Na$_2$SO$_4$. After filtration, the volatiles were removed under reduced pressure to afford the products as a pale yellow oil (41.1 g; 96% yield). $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.2 min (laurate).

Example 24

Preparation of 3-(4-(hydrogenated stripped cocoyloxy)-1-methylpiperidinium-1-yl)-2-hydroxypropanesulfonate To a 100-mL round bottom flask with a magnetic stir bar and a condenser was added N-methyl-4-piperidinyl hydrogenated stripped cocoate (5.00 g, 15.67 mmol), sodium 2-hydroxy-3-chloropropanesulfonate (ca. 90 wt %; 3.76 g, 17.24 mmol, 1.1 eq), sodium carbonate (166 mg; 1.57 mol; 0.10 equiv), and 1-methoxy-2-propanol (15 mL). The reaction mixture was heated to 110° C. for 12 hours to afford 99.0 area % conversion to product according to HPLC analysis. The mixture was filtered while warm (60° C.) to remove any precipitated solids, and the solids were washed with isopropanol. The combined filtrate and washes were concentrated at reduced pressure and in vacuo to afford 7.69 g of the product as an off-white solid. A portion (6.60 g) of this material was dried in a vacuum oven to afford 6.47 g of material that assayed at 96.9 wt % 3-(4-(hydrogenated stripped cocoyloxy)-1-methylpiperidinium-1-yl)-2-hydroxypropanesulfonate by HPLC. $^1$H NMR analysis was consistent with the product structure.

HPLC (150×4.6 mm Zorbax SB-C8 column, 75:25 (v:v) methanol:water (containing 0.1 vol % trifluoroacetic acid) for 10 min, gradient to 100% methanol over 1 min, held at 100% methanol for 9 min, ELSD detection): $t_R$ 4.7, 5.0 min (laurate).

Example 25

Preparation of N-methyl-4-piperdinyl Capric/Caprylic Ester

To a round bottom flask with a magnetic stir bar was added a 59:41 (w/w) mixture of capric acid and caprylic acid (20.8 g, 134 mmol), 4-hydroxy-N-methylpiperidine (20.0 g, 174 mmol; 1.3 equiv), heptane (10.5 mL), and Novozym 435 (2 g). A Dean-Stark apparatus was placed onto the flask, the mixture was heated to 65° C., and the reaction was placed under vacuum to distill the water/heptane azeotrope (heptane was returned to the flask via the Dean-Stark apparatus). The reaction was conducted until GC analysis indicated 99 area % conversion to the ester. The reaction was allowed to cool to ambient temperature, and the solids (Novozym 435) were removed by filtration and washed with heptane. The filtrate was washed with water and dried with Na$_2$SO$_4$. After filtration, the volatiles were removed under reduced pressure to afford the products as a pale yellow oil (32.7 g; 97% yield). $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, ELSD detection): $t_R$ 1.95 min (capric acid ester); 2.35 min (caprylic acid ester).

Example 26

Preparation of 3-(4-(caproyloxy/capryloyloxy)-1-methylpiperidinium-1-yl)-2-hydroxypropane-sulfonate To a 100-mL round bottom flask with a magnetic stir bar and a condenser was added N-methyl-4-piperidinyl capric/caprylic ester (5.00 g, 19.77 mmol), sodium 2-hydroxy-3-chloropropanesulfonate (ca. 90 wt %; 4.75 g, 21.75 mmol, 1.1 eq), sodium carbonate (210 mg; 1.98 mol; 0.10 equiv), and 1-methoxy-2-propanol (15 mL). The reaction mixture was heated to 110° C. for 20 hours to afford 99.0 area % conversion to product according to HPLC analysis. The mixture was cooled to ambient temperature, filtered to remove any precipitated solids, and the solids were washed with isopropanol. The combined filtrate and washes were concentrated at reduced pressure and in vacuo to afford 8.26 g of the product as an off-white solid. A portion (6.91 g) of this material was dried in a vacuum oven to afford 6.41 g of material. $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, ELSD detection): $t_R$ 2.10 min (capric acid ester); 2.62 min (caprylic acid ester).

Example 27

Preparation of 3-(3-(lauroyloxy)-1-butyldimethyl-ammonio-1-yl)-2-hydroxypropanesulfonate To a 4-L reactor equipped with a mechanical stirrer and a condenser was added 1-dimethylamino-3-butyl laurate (419.06 g, 1.40 mol), sodium 2-hydroxy-3-chloropropane-sulfonate (ca. 90 wt %; 336 g, 1.54 mol, 1.1 eq), sodium carbonate (14.83 g; 0.14 mol; 0.10 equiv), isopropanol (1260 mL), and water (210 mL). The reaction mixture was heated to reflux for 21 hours to afford 99.7 area % conversion to product according to HPLC analysis. The mixture was cooled to ambient temperature and filtered to remove any precipitated solids, and the solids were washed with isopropanol. The combined filtrate and washes were concentrated at reduced pressure, and the residue was treated with water (1428 mL) and the mixture was heated to 65° C. and purged (headspace) with nitrogen to remove residual isopropanol. This resulted in 2012 g of 3-(3-(lauroyloxy)-1-butyldimethylammonio-1-yl)-2-hydroxypropanesulfonate as a 25.9 wt % aqueous solution as indicated by wt % $^1$H NMR analysis. $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, gradient to 100% methanol over 1 min, held at 100% methanol for 9 min, ELSD detection): $t_R$ 3.78 min.

Example 28

Preparation of 3-(3-(hydrogenated cocoyloxy)-1-butyldimethylammonio-1-yl)-2-hydroxypropane-sulfonate To a 100-mL round bottom flask with a magnetic stir bar and a condenser was added 1-dimethylamino-3-butyl hydrogenated cocoate (2.50 g, 8.08 mmol), sodium 2-hydroxy-3-chloropropanesulfonate (ca. 90 wt %; 1.94 g, 8.88 mmol, 1.1 eq), sodium carbonate (86 mg; 0.81 mol; 0.10 equiv), isopropanol (7.5 mL), and water (1.25 mL). The reaction mixture was heated to reflux for 12 hours to afford 99.9 area % conversion to product according to HPLC analysis. The mixture was cooled to ambient temperature and filtered to remove any precipitated solids, and the solids were washed with isopropanol. The combined filtrate and washes were concentrated at reduced pressure and in vacuo to afford 3.91 g of the product as an off-white solid. $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, gradient to 100% methanol over 1 min, held at 100% methanol for 9 min, ELSD detection): $t_R$ 3.78 min (laurate).

Example 29

Preparation of 3-(3-(hydrogenated stripped cocoy-loxy)-1-butyldimethylammonio-1-yl)-2-hydroxypro-panesulfonate To a 100-mL round bottom flask with a magnetic stir bar and a condenser was added 1-dimethylamino-3-butyl hydrogenated stripped cocoate (5.00 g, 15.57 mmol), sodium 2-hydroxy-3-chloropropanesulfonate (ca. 90 wt %; 3.74 g, 17.12 mmol, 1.1 eq), sodium carbonate (165 mg; 1.56 mol; 0.10 equiv), isopropanol (15 mL), and water (2.5 mL). The reaction mixture was heated to reflux for 12 hours to afford 99.9 area % conversion to product according to HPLC analysis. The mixture was cooled to ambient temperature and filtered to remove any precipitated solids and the solids were washed with isopropanol. The combined filtrate and washes were concentrated at reduced pressure and in vacuo to afford 7.60 g of the product as an off-white solid. $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, gradient to 100% methanol over 1 min, held at 100% methanol for 9 min, ELSD detection): $t_R$ 3.78 min (laurate).

Example 30

Preparation of 3-(3-(caproyloxy/capryloyloxy)-1-butyldimethylammonio-1-yl)-2-hydroxypropane-sulfonate To a 100-mL round bottom flask with a magnetic stir bar and a condenser was added 1-dimethylamino-3-butyl capric/caprylic ester (2.50 g, 9.81 mmol), sodium 2-hydroxy-3-chloropropanesulfonate (ca. 90 wt %; 2.36 g, 10.79 mmol, 1.1 eq), sodium carbonate (104 mg; 0.98 mol; 0.10 equiv), isopropanol (7.5 mL), and water (1.25 mL). The reaction mixture was heated to reflux for 12 hours to afford 99.8 area % conversion to product according to HPLC analysis. The mixture was cooled to ambient temperature and filtered to remove any precipitated solids, and the solids were washed with isopropanol. The combined filtrate and washes were concentrated at reduced pressure and in vacuo to afford 4.18 g of the product as an off-white solid. $^1$H NMR analysis was consistent with the product structure.

HPLC (150×4.6 mm Zorbax SB-C8 column, 80:20 (v:v) methanol:water (containing 0.1 vol % trifluoroacetic acid) for 10 min, ELSD detection): $t_R$ 2.15 min (capric acid ester); 2.68 min (caprylic acid ester).

Surfactant Properties

The surfactant properties of the compounds of the formula 1 can be determined by a number of tests including an ASTM foam height test and a test for critical micelle concentration.

The Standard Test Method for Foaming Properties of Surface-Active Agents (ASTM 1173-07) was used to determine the foaming properties of the ester sulfonates 1 described herein. This method generates foam under low-agitation conditions and is generally used for moderate- and high-foam surfactants. This test gathers data on initial foam height and foam decay.

Foam decay provides information on foam stability.

The apparatus for carrying out this test includes a jacketed column and a pipet. The jacketed column serves as a receiver, while the pipet delivers the surface-active solution. Solutions of each surface-active agent were prepared. The amphoteric ester sulphonate solution to be tested was added to the receiver (50 mL) and to the pipet (200 mL). The pipet was positioned above the receiver and opened. As the solution fell and made contact with the solution in the receiver, foam was generated. When the pipet was empty, the time was noted and an initial foam height was recorded. The foam height was recorded each minute for five minutes. Exact size specifications for the glassware can be found in ASTM 1173-07. The foam height results for each ester sulfonate 1 and representative standards are listed below in Tables 1 (0.1% concentration) and 2 (1% concentration).

The critical micelle concentration (CMC) was also determined for each compound. The CMC is the concentration of surfactant above which micelles spontaneously form. CMC is an important characteristic of a surfactant. At surfactant concentrations below the CMC, surface tension varies widely with surfactant concentration. At concentrations above the CMC, surface tension remains fairly constant. A lower CMC indicates less surfactant is needed to saturate interfaces and form micelles. Typical CMC values are less than 1 weight percent (10,000 ppm).

The fluorimetric determination of CMC described by Chattopadhyay and London (*Analytical Biochemistry*, Vol. 139, pp. 408-412 (1984)) was used to obtain the critical micelle concentrations found in Table 3 below. This method employs the fluorescent dye 1,6-diphenyl-1,3,5-hexatriene (DPH) in a solution of the surface-active agent. The analysis is based on differences in fluorescence upon incorporation of the dye into the interior of the micelles. As the solution exceeds CMC, a large increase in fluorescence intensity is observed. This method has been found to be sensitive and reliable, and has been demonstrated on zwitterionic, anionic, cationic, and uncharged surface-active agents.

TABLE 1

Foam height (cm) at time t (min) at 0.1 wt % concentration

| | Foam height (cm) at time t (min) 1 g/L (0.1 weight %) | | | | | |
|---|---|---|---|---|---|---|
| | t = 0 | 1 | 2 | 3 | 4 | 5 |
| Standard | | | | | | |
| cocamidopropyl betaine | 17.0 | 16.0 | 16.0 | 16.0 | ND | 15.5 |
| Compound from Example No. | | | | | | |
| 3 | 16.0 | 15.5 | 15.5 | 15.0 | 15.0 | 13.5 |
| 4 | 15.5 | 15.5 | 15.0 | 14.5 | 14.5 | 14.5 |
| 6 | 11.0 | 7.5 | 3.0 | 1.0 | 1.0 | 1.0 |
| 8 | 11.5 | 10 | 7.5 | 3.0 | 1.5 | 1.5 |
| 9 | 14.5 | 14.0 | 14.0 | 14.0 | 13.5 | 13.5 |
| 10 | 16.5 | 16.0 | 15.5 | 15.5 | 15.5 | 15.5 |
| 12 | 16.5 | 16.0 | 16.0 | 16.0 | 15.5 | 15.5 |
| 14 | 16.5 | 16.0 | 16.0 | 15.5 | 15.5 | 15.0 |
| 22 | 12.0 | 11.5 | 11.5 | 11.5 | 11.5 | 11.5 |
| 24 | 15.5 | 15.0 | 15.0 | 15.0 | 15.0 | 15.0 |
| 26 | 5.0 | 4.5 | 4.0 | 3.5 | 3.5 | 3.0 |
| 27 | 16.5 | 16.0 | 15.5 | 15.5 | 15.5 | 15.0 |
| 28 | 16.5 | 15.5 | 15.5 | 15.5 | 15.5 | 15.5 |
| 29 | 14.5 | 14.5 | 14.0 | 14.0 | 14.0 | 14.0 |
| 30 | 13.0 | 11.5 | 10.0 | 9.0 | 7.0 | 4.0 |

ND = not determined

TABLE 2

Foam height (cm) at time t (min) at 1.0 wt % concentration

| | Foam height (cm) at time t (min) 10 g/L (1.0 weight %) | | | | | |
|---|---|---|---|---|---|---|
| | t = 0 | 1 | 2 | 3 | 4 | 5 |
| Standard | | | | | | |
| cocamidopropyl betaine | 17.5 | 16.5 | ND | 16.0 | 16.0 | 16.0 |
| Compound from Example No. | | | | | | |
| 3 | 17.5 | 16.5 | 16.5 | 16.0 | 14.0 | 14.0 |
| 4 | 16.5 | 16.0 | 15.5 | 15.0 | 14.5 | 14.5 |
| 6 | 18.5 | 16.0 | 15.0 | 13.0 | 9.0 | 3.0 |
| 8 | 18.5 | 17.5 | 16.5 | 15.5 | 14.5 | 12.0 |
| 9 | 18.5 | 18.0 | 17.0 | 16.5 | 16.5 | 15.5 |
| 10 | 18.5 | 17.5 | 17.0 | 16.5 | 16.5 | 16.0 |
| 12 | 18.5 | 17.5 | 17.5 | 17.0 | 17.0 | 16.5 |
| 14 | 17.5 | 17.0 | 17.0 | 17.0 | 16.5 | 16.5 |
| 22 | 18.0 | 17.5 | 17.0 | 16.5 | 16.0 | 16.0 |
| 24 | 17.0 | 16.5 | 16.5 | 16.0 | 16.0 | 16.0 |
| 26 | 16.5 | 15.0 | 12.0 | 3.0 | 1.0 | 1.0 |
| 27 | 17.5 | 17.0 | 17.0 | 16.5 | 16.0 | 15.5 |
| 28 | 17.0 | 16.5 | 16.0 | 16.0 | 16.0 | 15.5 |
| 29 | 17.5 | 17.0 | 17.0 | 16.5 | 16.5 | 16.0 |
| 30 | 17.5 | 17.0 | 16.5 | 16.0 | 15.5 | 15.0 |

ND = not determined

As the data in Tables 1 and 2 indicate, solutions of the amphoteric ester sulfonates 1 generate large amounts of foam. Examples in which the foam height does not decrease over time indicate good foam stability.

TABLE 3

Critical micelle concentrations

| | CMC (ppm) | CMC (mM) |
|---|---|---|
| Standards | | |
| sodium lauryl sulfate | 2386 | 8.27 |
| ammonium lauryl sulfate | 392 | 1.38 |
| cocamidopropyl betaine | 24.5 | 0.069 |
| Compound from Example No. | | |
| 3 | 20.9 | 0.048 |
| 4 | 32.9 | 0.078 |
| 6 | 17.8 | 0.041 |
| 8 | 15.3 | 0.036 |
| 9 | 30.8 | 0.071 |
| 10 | 36.9 | 0.091 |
| 12 | 33.3 | 0.074 |
| 14 | 26.0 | 0.056 |
| 27 | 26.4 | 0.060 |

The data in Table 3 indicate that very low concentrations of the amphoteric ester sulfonates 1 are needed to reach the critical micelle concentration. These values fall in the range of useful surface-active agents, and compare well with standard surfactants.

Stability Properties

It has been unexpectedly found that the amphoteric ester sulfonates of the present invention are significantly more stable at low pH aqueous conditions than the corresponding amphoteric ester betaines disclosed in US 2012/0277324 A1. The amphoteric ester sulfonates exhibited little loss of the amphoteric under extended incubation in pH 4.5 water at 50° C., while the similar ester betaine showed significant assay loss of the amphoteric, even under less harsh conditions.

Comparative Example 1

Preparation of
3-(cocoyloxypropyldimethylammonio)acetate

To a 3-L reactor equipped with a condenser and an overhead stirrer was added 3-dimethylaminopropyl cocoate (350.42 g; 1.21 mol), sodium chloroacetate (155 g, 1.33 mol, 1.1 eq), sodium bicarbonate (20.32 g; 0.24 mol; 0.2 equiv), and water (807 g). The reaction mixture was stirred and heated to an internal temperature of 76° C. for 12 hours to afford >98% conversion according to HPLC analysis. The mixture was cooled to ambient temperature, and the pH was adjusted to 6.5 by adding 3 M HCl. The resulting mixture was clarified to afford 1267 g of a clear yellow liquid. Analysis of the mixture by HPLC indicated a 29.6 wt % solution of 3-(cocoyloxypropyldimethylammonio)acetate in water. $^1$H NMR analysis was consistent with the product structure.

HPLC (150×4.6 mm Zorbax SB-C8 column, 80:20 methanol:water (containing 0.1% trifluoroacetic acid) for 10 min, gradient to 100% methanol over 1 min, held at 100% methanol for 9 min, ELSD detection): $t_R$ (laurate ester) 3.5 min.

Example 31

Stability Study of 3-(lauroyloxypropyldimethylammonio)-2-hydroxypropanesulfonate The product from Example 16 (20 mL) was combined with 210 mg of citric acid hydrate, and the pH was lowered to 4.5 by adding aqueous HCl. The resulting mixture was placed in a 50° C. oven. Samples were taken periodically and analyzed for the amount of 3-(lauroyloxypropyldimethylammonio)-2-hydroxypropanesulfonate remaining by quantitative HPLC. The results are reported in Table 4 below.

Comparative Example 2

Stability Study of 3-(cocoyloxypropyldimethylammonio)acetate

The product from Comparative Example 1 was adjusted to a pH of 5 by adding aqueous HCl and then placed in a 45° C. oven. Samples were taken periodically and analyzed for the amount of 3-(cocoyloxypropyldimethylammonio)acetate remaining by quantitative HPLC. The results are in Table 4 below.

TABLE 4

Comparative stability of ester carboxy and ester sulfonate amphoterics

| | Percent Amphoteric Remaining | |
| --- | --- | --- |
| | Example 31 (ester sulfonate amphoteric) | Comparative Example 2 (ester carboxy amphoteric) |
| Conditions | pH 4.5, 50° C. | pH 5, 45° C. |
| Time (weeks) | | |
| 0 | 100% | 100% |
| 2 | 98% | 74% |
| 6 | 98% | ND |
| 8 | 94% | 73% |
| 12 | 95% | 53% |

ND = not determined

The invention has been described in detail with particular reference to preferred embodiments thereof, but it will be understood that variations and modifications can be effected within the spirit and scope of the invention.

We claim:
1. A compound having the formula 1:

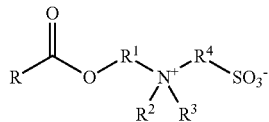

wherein
R is $C_3$-$C_{23}$ hydrocarbyl;
$R^1$ is branched $C_3$-$C_8$ hydrocarbyl;
$R^2$ and $R^3$ are each independently selected from the group consisting of $C_1$-$C_6$ alkyl, $C_1$-$C_6$ alkenyl, $C_1$-$C_6$ dienyl, $C_1$-$C_6$ trienyl, and $C_3$-$C_8$ cycloalkyl; and
$R^4$ is $C_1$-$C_8$ hydrocarbyl substituted with a hydroxyl group.

2. The compound according to claim 1, wherein
R is selected from the group consisting of $C_5$-$C_{19}$ alkyl, $C_5$-$C_{17}$ alkenyl, $C_5$-$C_{17}$ dienyl, and $C_3$-$C_8$ cycloalkyl;
$R^2$ and $R^3$ are each independently selected from the group consisting of $C_1$-$C_6$ alkyl and $C_1$-$C_6$ alkenyl; and
$R^4$ is $C_1$-$C_8$ alkylene substituted with a hydroxyl group.

3. The compound according to claim 1, wherein
RCO— is octanoyl, decanoyl, lauroyl, or a $C_6$ to $C_{20}$ acyl radical derived from coconut oil, hydrogenated coconut oil, hydrogenated and/or fractionated coconut oil fatty acids, palm kernel oil, hydrogenated palm kernel oil, or hydrogenated and/or fractionated palm kernel oil fatty acids;
$R^1$ is 1,3-butylene;
$R^2$ and $R^3$ are methyl; and
$R^4$ is 2-hydroxy-1,3-propylene.

4. A process for preparing a compound having the formula 1:

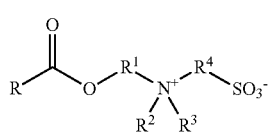

wherein
R is $C_3$-$C_{23}$ hydrocarbyl;
$R^1$ is branched $C_3$-$C_8$ hydrocarbyl;
$R^2$ and $R^3$ are each independently selected from the group consisting of $C_1$-$C_6$ alkyl, $C_1$-$C_6$ alkenyl, $C_1$-$C_6$ dienyl, $C_1$-$C_6$ trienyl, and $C_3$-$C_8$ cycloalkyl; and
$R^4$ is $C_1$-$C_8$ hydrocarbyl substituted with a hydroxyl group,
the process comprising:
(a) contacting an acid or ester of formula 2 with a dialkylamino-alcohol of formula 3:

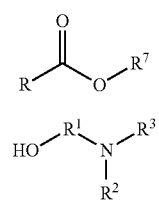

in the presence of an enzyme at conditions effective to form an intermediate of formula 4:

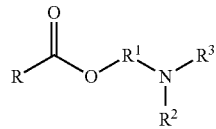

wherein R, $R^1$, $R^2$, and $R^3$ are as defined above and $R^7$ is hydrogen or $C_1$-$C_6$ alkyl; and (b) contacting the intermediate of formula 4 with a sulfonate alkylating agent at conditions effective to form the compound of formula 1.

5. The process according to claim 4, wherein the enzyme is a lipase from *Pseudomonas* sp or *Candida antarctica*.

6. The process according to claim 4, wherein step (a) is carried out at a temperature of 50 to 70° C. and a pressure of 10 Torr (1,333 Pa) to ambient pressure, and wherein step (b) is carried out at a temperature of 50 to 125° C.

7. The process according to claim 4, which further comprises removing water or alcohol by-product from the reaction mixture during step (a).

8. The process according to claim 4, wherein step (b) is carried out in the presence of a base selected from the group consisting of metal hydroxides, metal carbonates, and metal bicarbonates; and wherein step (b) is carried out in the presence of a solvent selected from the group consisting of water, $C_2$-$C_5$ alcohols, ether-alcohols, and mixtures thereof.

9. The process according to claim 4, wherein the sulfonate alkylating agent is sodium 3-chloro-2-hydroxypropane-sulfonate.

10. The process according to claim 4, wherein
R is selected from the group consisting of $C_5$-$C_{19}$ alkyl, $C_5$-$C_{17}$ alkenyl, $C_5$-$C_{17}$ dienyl, and $C_3$-$C_8$ cycloalkyl;
$R^2$ and $R^3$ are each independently selected from the group consisting of $C_1$-$C_6$ alkyl and $C_1$-$C_6$ alkenyl; and
$R^4$ is $C_1$-$C_8$ alkylene substituted with a hydroxyl group.

11. The process according to claim 4, wherein
RCO— is octanoyl, decanoyl, lauroyl, or a $C_6$ to $C_{20}$ acyl radical derived from coconut oil, hydrogenated coconut oil, hydrogenated and/or fractionated coconut oil fatty acids, palm kernel oil, hydrogenated palm kernel oil, or hydrogenated and/or fractionated palm kernel oil fatty acids;
$R^1$ is 1,3-butylene;
$R^2$ and $R^3$ are methyl; and
$R^4$ is 2 hydroxy-1,3-propylene.

\* \* \* \* \*